United States Patent
Jaehne et al.

(10) Patent No.: US 6,387,935 B1
(45) Date of Patent: *May 14, 2002

(54) POLYCYCLIC DIHYDROTHIAZOLES HAVING SUBSTITUTED ALKYL RADICALS IN THE TWO-POSITION, PROCESS FOR THEIR PREPARATION, AND THEIR USE AS PHARMACEUTICALS

(75) Inventors: Gerhard Jaehne, Frankfurt; Matthias Gossel, Hofheim; Hans-Jochen Lang, Hofheim; Martin Bickel, Bad Homburg, all of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/706,351

(22) Filed: Nov. 6, 2000

(30) Foreign Application Priority Data

Nov. 5, 1999 (DE) .......................... 199 53 205
Mar. 17, 2000 (DE) .......................... 100 13 306

(51) Int. Cl.[7] .................. A61K 31/428; A61K 31/429; C07D 277/60
(52) U.S. Cl. ........................................ 514/366; 548/150
(58) Field of Search .......................... 548/150; 514/366

(56) References Cited

U.S. PATENT DOCUMENTS 3,507,868 A   4/1970   Manning et al.
6,090,833 A * 7/2000   Jaehne et al. ............. 514/366

FOREIGN PATENT DOCUMENTS

| DE | 26 40 358 | 3/1978 |
| WO | WO 00/04006 | 1/2000 |
| WO | WO 00/18749 | 4/2000 |
| WO | WO 00/51994 | 9/2000 |

* cited by examiner

Primary Examiner—Laura L. Stockton
(74) Attorney, Agent, or Firm—Heller Ehrman White & McAuliffe

(57) ABSTRACT

The invention relates to polycyclic dihydrothiazoles, and to their physiologically acceptable salts and physiologically functional derivatives. The compounds are according to formula I:

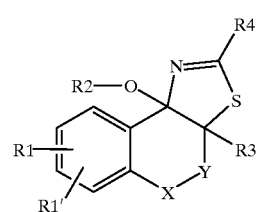

in which the radicals have the meanings indicated, and their physiologically acceptable salts and process for their preparation are described. The compounds are suitable, for example, for use as anorectics.

33 Claims, No Drawings

POLYCYCLIC DIHYDROTHIAZOLES HAVING SUBSTITUTED ALKYL RADICALS IN THE TWO-POSITION, PROCESS FOR THEIR PREPARATION, AND THEIR USE AS PHARMACEUTICALS

FIELD OF THE INVENTION

The invention relates to polycyclic dihydrothiazoles and their physiologically acceptable salts and physiologically functional derivatives. The polycyclic dihydrothiazoles are useful in the treatment and prophylaxis of obesity and type II diabetes.

BACKGROUND OF THE INVENTION

Thiazolidine derivatives having anorectic action have already been described in the prior art (Austrian Patent No. 365181).

The invention is based on the object of making available further compounds which display a therapeutically utilizable anorectic action.

SUMMARY OF THE INVENTION

The invention relates to compounds of the formula I:

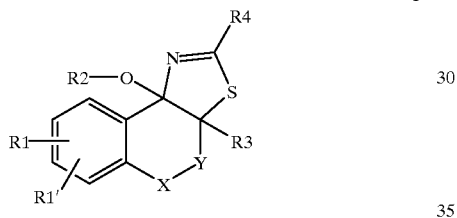

in which
Y is selected from the group consisting of a direct bond, —CH$_2$—, and —CH$_2$—CH$_2$—;
X is selected from the group consisting of CH$_2$, CH(CH$_3$), CH(C$_2$H$_5$), CH(C$_3$H$_7$), and CH(C$_6$H$_5$);
R1, R1' are independently selected from the group consisting of H, F, Cl, Br, I, CF$_3$, NO$_2$, CN, COOH, COO(C$_{1-6}$)alkyl, CONH$_2$, CONH(C$_{1-6}$)alkyl, CON[(C$_{1-6}$)alkyl]$_2$, (C$_{1-6}$)alkyl, (C$_2$–C$_6$)-alkenyl, (C$_2$–C$_6$)-alkynyl, O—(C$_1$–C$_6$)-alkyl,
wherein one or more of the hydrogens in the alkyl moieties may be optionally replaced by fluorine,
or a hydrogen may be optionally replaced by OH, OC(O)CH$_3$, OC(O)H, O—CH$_2$—Ph, NH$_2$, NH—CO—CH$_3$ or N(COOCH$_2$Ph)$_2$,
SO$_2$—NH$_2$, SO$_2$NH(C$_{1-C6}$)-alkyl, SO$_2$N[(C$_{1-C6}$)-alkyl]$_2$, S—(C$_{1-C6}$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl,
where n is 0–6 and wherein the phenyl radical is optionally substituted in up to two positions by F, Cl, Br, OH, CF$_3$, NO$_2$, CN, OCF$_3$, O—(C$_1$–C$_6$)-alkyl, (C$_1$–C$_6$)-alkyl, or NH$_2$;
NH$_2$, NH—(C$_1$–C$_6$)-alkyl, N((C$_1$–C$_6$)-alkyl)$_2$, NH(C$_1$–C$_7$)-acyl, phenyl, biphenyl, O—(CH$_2$)$_n$-phenyl, where n is 0–6, 1- or 2-naphthyl, 2-, 3- or 4-pyridyl, 2- or 3-furanyl, 2- or 3-thienyl,
wherein the phenyl, biphenyl, naphthyl, pyridyl, furanyl or thienyl rings may be independently optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl, or CONH$_2$;
1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;
R2 is selected from the group consisting of H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl and C(O)—(CH$_2$)$_n$-furyl, where n is 0–5,
wherein the phenyl, thienyl, pyridyl, or furyl ring may be optionally substituted up to two times by Cl, F, CN, CF$_3$, (C$_1$–C$_3$)-alkyl, OH or O—(C$_1$–C$_6$)-alkyl;
R3 is selected from the group consisting of H, (C$_1$–C$_6$)-alkyl, F, CN, N$_3$, O—(C$_1$–C$_6$)-alkyl, (CH$_2$)$_n$-phenyl, (CH$_2$)$_n$-thienyl, (CH$_2$)$_n$-pyridyl and (CH$_2$)$_n$-furyl, where n is 0–5,
wherein the phenyl, thienyl, pyridyl, or furyl ring may be optionally substituted up to two times by Cl, F, CN, CF$_3$, (C$_1$–C$_3$)-alkyl, OH or O—(C$_1$–C$_6$)-alkyl, (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, or OC(O)CH$_3$;
R4 is selected from the group consisting of (C$_8$–C$_{16}$)-cycloalkyl,
wherein one or more hydrogens of the alkyl moiety may be optionally replaced by fluorine,
or a hydrogen may be optionally replaced by OH, OC(O)CH$_3$, OC(O)H, O—CH$_2$—Ph or O—(C$_1$–C$_4$)-alkyl;
(CH$_2$)$_n$—A—R8, where n is 1–6, except for when (CH$_2$)$_n$—A—R8 is —CH$_2$—O—CH$_2$-phenyl, then the phenyl moiety is unsubstituted; and
(CH$_2$)$_r$—B—R9, where r is 1–6;
A is selected from the group consisting of O, S, SO and SO$_2$;
B is selected from the group consisting of NH, N—(C$_1$–C$_6$)-alkyl, NCHO and N(CO—CH$_3$);
R8 is selected from the group consisting of (C$_5$–C$_{24}$)-alkyl, (C$_3$–C$_{10}$)-cycloalkyl,
wherein one or more hydrogens of the alkyl radical may be optionally replaced by fluorine,
or a hydrogen may be optionally replaced by OH, OC(O)CH$_3$, OC(O)H, O—CH$_2$—Ph or O—(C$_{1-C4}$)-alkyl; and
(CH$_2$)$_m$-aryl, where m is 0–6 and aryl is selected from the group consisting of phenyl, naphthyl, biphenyl, thienyl and pyridyl;
wherein the aryl moiety may be optionally substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, SO$_2$—NH$_2$, SO$_2$—NH(C$_1$–C$_8$-alkyl), SO$_2$—N(C$_1$–C$_8$-alkyl)$_2$, SO$_2$—NH(C$_3$–C$_8$-cycloalkyl), SO$_2$—N (C$_3$–C$_8$-cycloalkyl)$_2$, (CH$_2$)m—SO$_2$—NH$_2$, (CH$_2$)$_m$—SO$_2$—NH—(C$_1$–C$_6$)-alkyl, (CH$_2$)$_m$—SO$_2$—N ((C$_1$–C$_6$)-alkyl)$_2$, where m is 1–6, SO$_2$—N(=CH—N(CH$_3$)$_2$), (C$_1$–C$_6$)-alkyl, (C$_3$–C$_6$)-cycloalkyl, COOH, COO(C$_1$–C$_6$)alkyl, COO (C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$) cycloalkyl, NH$_2$, NH(C$_1$–C$_6$)-alkyl, N(C$_1$–C$_6$-alkyl)$_2$, NH—CO—($C_1$-$C_6$)-alkyl, NH—CO-phenyl, NH—$SO_2$—($C_1$-$C_8$-alkyl), N($C_1$-$C_6$-alkyl)—$SO_2$—($C_1$-$C_8$-alkyl), NH—$SO_2$-phenyl, wherein the phenyl ring may be optionally substituted up to two times by F, Cl, CN, OH, ($C_1$-$C_6$)-alkyl, O—($C_1$-$C_6$)-alkyl, $CF_3$, COOH, COO($C_1$-$C_6$)-alkyl or $CONH_2$, pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$-$(CH_2)_p$-phenyl, where p is 0–3;

R9 is $(CH_2)_m$-aryl, where m is 0–6 and aryl is selected from the group consisting of phenyl, naphthyl, biphenyl, thienyl and pyridyl;

wherein the aryl moiety may be optionally substituted up to two times by F, Cl, Br, OH, $CF_3$, $NO_2$, CN, $OCF_3$, O—($C_1$-$C_6$)-alkyl, S—($C_1$-$C_6$)-alkyl, SO—($C_1$-$C_6$)-alkyl, $SO_2$—($C_1$-$C_6$)-alkyl, $SO_2$—$NH_2$, $SO_2$—NH($C_1$-$C_8$-alkyl), $SO_2$—N($C_1$-$C_8$-alkyl)$_2$, $SO_2$—NH($C_3$-$C_8$-cycloalkyl), $SO_2$—N($C_3$-$C_8$-cycloalkyl)$_2$, $(CH_2)m$—$SO_2$—$NH_2$, $(CH_2)_m$—$SO_2$—NH—($C_1$-$C_6$)-alkyl, $(CH_2)_m$—$SO_2$—N(($C_1$-$C_6$)-alkyl)$_2$, where m is 1–6, $SO_2$—N(=CH—N $(CH_3)_2$), ($C_1$-$C_6$)-alkyl, ($C_3$-$C_6$)-cycloalkyl, COOH, COO($C_1$-$C_6$)alkyl, COO($C_3$-$C_6$)cycloalkyl, $CONH_2$, CONH($C_1$-$C_6$) alkyl, CON[($C_1$-$C_6$)alkyl]$_2$, CONH($C_3$-$C_6$) cycloalkyl, $NH_2$, NH($C_1$-$C_6$)-alkyl, N($C_1$-$C_6$-alkyl)$_2$, NH—CO—($C_1$-$C_6$)-alkyl, NH—CO-phenyl, NH—$SO_2$—($C_1$-$C_8$-alkyl), N($C_1$-$C_6$-alkyl)—$SO_2$—($C_1$-$C_8$-alkyl), NH—$SO_2$-phenyl, wherein the phenyl ring may be optionally substituted up to two times by F, Cl, CN, OH, ($C_1$-$C_6$)-alkyl, O—($C_1$-$C_6$)-alkyl, $CF_3$, COOH, COO($C_1$-$C_6$)-alkyl or $CONH_2$, pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, where p is 0–3;

and a physiologically acceptable salt thereof.

The invention also relates to pharmaceutical compositions comprising the compounds of formula I, methods for treatment or prophylaxis or obesity, methods for treatment or prophylaxis of type II diabetes. The invention also contemplates administration of a compound of formula I in combination with an additional anorectic active agent useful in the treatment or prophylaxis or obesity or type II diabetes. The invention also envisages a process for preparing the pharmaceutical composition and also a process for synthesizing the inventive compounds of formula I.

Additional objects, features and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The invention relates to compounds of the formula I:

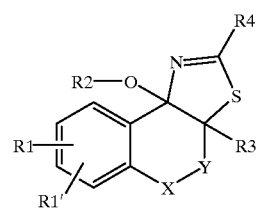

I in which

Y is selected from the group consisting of a direct bond, —$CH_2$-, and —$CH_2$—$CH_2$-;

X is selected from the group consisting of $CH_2$, CH($CH_3$), CH($C_2H_5$), CH($C_3H_7$), and CH($C_6H_5$);

R1, R1' are independently selected from the group consisting of H, F, Cl, Br, I, $CF_3$, $NO_2$, CN, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, wherein one or more of the hydrogens in the alkyl moieties may be optionally replaced by fluorine, or a hydrogen may be optionally replaced by OH, OC(O)$CH_3$, OC(O)H, O—$CH_2$—Ph, $NH_2$, NH—CO—$CH_3$ or N($COOCH_2$Ph)$_2$, $SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—$(CH_2)_n$-phenyl, SO—($C_1$-$C_6$)-alkyl, SO—$(CH_2)_n$-phenyl, $SO_2$-($C_1$-$C_6$)-alkyl, $SO_2$-$(CH_2)_n$-phenyl, where n is 0–6 and wherein the phenyl radical is optionally substituted in up to two positions by F, Cl, Br, OH, $CF_3$, $NO_2$, CN, $OCF_3$, O—($C_1$-$C_6$)-alkyl, ($C_1$-$C_6$)-alkyl, or $NH_2$;

$NH_2$, NH—($C_1$-$C_6$)-alkyl, N(($C_1$-$C_6$)-alkyl)$_2$, NH($C_1$-$C_7$)-acyl, phenyl, biphenyl, O—$(CH_2))_n$-phenyl, where n is 0–6, 1- or 2-naphthyl, 2-, 3- or 4-pyridyl, 2- or 3-furanyl, 2- or 3-thienyl, wherein the phenyl, biphenyl, naphthyl, pyridyl, furanyl or thienyl rings may be independently optionally substituted up to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, or $CONH_2$;

1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;

R2 is selected from the group consisting of H, ($C_1$-$C_6$)-alkyl, ($C_3$-$C_6$)-cycloalkyl, $(CH_2)_n$-phenyl, $(CH_2)_n$-thienyl, $(C_2)_n$-pyridyl, $(CH_2)_n$-furyl, C(O)—($C_1$-$C_6$)-alkyl, C(O)—($C_3$-$C_6$)-cycloalkyl, C(O)—$(CH_2)_n$-phenyl, C(O)—$(CH_2)_n$-thienyl, C(O)—$(CH_2)_n$-pyridyl and C(O)—$(CH_2)_n$-furyl, where n is 0–5, wherein the phenyl, thienyl, pyridyl, or furyl ring may be optionally substituted up to two times by Cl, F, CN, $CF_3$, ($C_1$-$C_3$)-alkyl, OH or O—($C_1$-$C_6$)-alkyl;

R3 is selected from the group consisting of H, ($C_1$-$C_6$)-alkyl, F, CN, $N_3$, O—($C_1$-$C_6$)-alkyl, $(CH_2)_n$-phenyl, $(CH_2)_n$-thienyl, $(CH_2)_n$-pyridyl and $(CH_2)_n$-furyl, where n is 0–5, wherein the phenyl, thienyl, pyridyl, or furyl ring may be optionally substituted up to two times by Cl, F, CN, CF$_3$, (C$_1$–C$_3$)-allyl, OH or O—(C$_1$–C$_6$)-allyl, (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, or OC(O)CH$_3$;

R4 is selected from the group consisting of (C$_8$–C$_{16}$)-cycloalkyl,
  wherein one or more hydrogens of the alkyl moiety may be optionally replaced by fluorine,
  or a hydrogen may be optionally replaced by OH, OC(O)CH$_3$, OC(O)H, O—CH$_2$—Ph or O—(C$_1$–C$_4$)-alkyl;

(CH$_2$)$_n$—A—R8, where n is 1–6, except for when (CH$_2$)$_n$—A—R8 is —CH$_2$—O—CH$_2$-phenyl, then the phenyl moiety is unsubstituted; and (CH$_2$)$_r$—B—R9, where r is 1–6;

A is selected from the group consisting of O, S, SO and SO$_2$;

B is selected from the group consisting of NH, N—(C$_1$–C$_6$)-alkyl, NCHO and N(CO—CH$_3$);

R8 is selected from the group consisting of (C$_5$–C$_{24}$)-alkyl, (C$_3$–C$_{10}$)-cycloalkyl,
  wherein one or more hydrogens of the alkyl radical may be optionally replaced by fluorine,
  or a hydrogen may be optionally replaced by OH, OC(O)CH$_3$, OC(O)H, O—CH$_2$—Ph or O—(C$_1$–C$_4$)-alkyl; and (CH$_2$)$_m$-aryl, where m is 0–6 and aryl is selected from the group consisting of phenyl, naphthyl, biphenyl, thienyl and pyridyl;
  wherein the aryl moiety may be optionally substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, SO$_2$—NH$_2$, SO$_2$—NH(C$_1$–C$_8$-alkyl), SO$_2$—N(C$_1$–C$_8$-alkyl)$_2$, SO$_2$—NH(C$_3$–C$_8$-cycloalkyl), SO$_2$—N(C$_3$–C$_8$-cycloalkyl)$_2$, (CH$_2$)m—SO$_2$—NH$_2$, (CH$_2$)$_m$—SO—NH—(C$_1$-C$_6$)-alkyl, (CH$_2$)$_m$—SO$_2$—N((C$_1$–C$_6$)-alkyl)$_2$, where m is 1–6, SO$_2$—N(=CH—N(CH$_3$)$_2$), (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$) alkyl, CON[(C$_1$–C$_6$)alkyl]$_2$, CONH(C$_3$–C$_6$) cycloalkyl, NH$_2$, NH(C$_1$–C$_6$)-alkyl, N(C$_1$–C$_6$-alkyl)$_2$, NH—CO—(C$_1$–C$_6$)-alkyl, NH—CO-phenyl, NH—SO$_2$—(C$_1$–C$_8$-alkyl), N(C$_1$–C$_6$-alkyl)—SO$_2$—(C$_1$–C$_8$-alkyl), NH—SO$_2$-phenyl,
    wherein the phenyl ring may be optionally substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$,
  pyrrolidin-1-yl, morpholin-1-yl, piperidin-1-yl, piperazin-1-yl, 4-methylpiperazin-1-yl, (CH$_2$)$_p$-phenyl, O—(CH$_2$) $_p$-phenyl, S—(CH$_2$)$_p$-phenyl or SO$_2$—(CH$_2$)$_p$-phenyl, where p is 0–3;

R9 is (CH$_2$)$_m$-aryl, where m is 0–6 and aryl is selected from the group consisting of phenyl, naphthyl, biphenyl, thienyl and pyridyl;
  wherein the aryl moiety may be optionally substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, SO$_2$—NH$_2$, SO$_2$—NH(C$_1$–C$_8$-alkyl), SO$_2$—N(C$_1$–C$_8$-alkyl)$_2$, SO$_2$—NH(C$_3$–C$_8$-cycloalkyl), SO$_2$—N(C$_3$–C$_8$-cycloalkyl)$_2$, (CH$_2$)m—SO$_2$—NH$_2$, (CH$_2$)$_m$—SO$_2$—NH—(C$_1$-C$_6$)-alkyl, (CH$_2$)$_m$—SO$_2$—N((C$_1$–C$_6$)-alkyl)$_2$, where m is 1–6, SO$_2$—N(=CH—N(CH$_3$)$_2$), (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$) alkyl, CON[(C$_1$–C$_6$)alkyl]$_2$, CONH(C$_3$–C$_6$) cycloalkyl, NH$_2$, NH(C$_1$–C$_6$)-alkyl, N(C$_1$–C$_6$-alkyl)$_2$, NH—CO—(C$_1$–C$_6$)-alkyl, NH—CO-phenyl, NH—SO$_2$—(C$_1$–C$_8$-alkyl), N(C$_1$–C$_6$-alkyl)—SO$_2$—(C$_1$–C$_8$-alkyl), NH—SO$_2$-phenyl,
    wherein the phenyl ring may be optionally substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$,
  pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;

and a physiologically acceptable salt thereof.

A preferred embodiment of the invention relates to compounds of formula I where

Y is a direct bond;

X is CH$_2$;

R1, R1' are independently selected from the group consisting of H, F, Cl, Br, I, CF$_3$, NO$_2$, CN, COOH, COO(C$_1$–C$_6$)alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_1$–C$_6$)-alkyl,
  wherein one or more hydrogens of the alkyl radical may be optionally replaced by fluorine,
  or a hydrogen may be optionally replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$-(CH$_2$)$_n$-phenyl,
  where n is 0–6 and wherein the phenyl radical is optionally substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$;

NH$_2$, NH—(C$_1$–C$_6$)-alkyl, N((C$_1$–C$_6$)-alkyl)$_2$, NH(C$_1$–C$_7$)-acyl, phenyl, biphenyl, O—(CH$_2$)$_n$-phenyl, where n is 0–6, 1- or 2-naphthyl, 2-, 3- or 4-pyridyl, 2- or 3-furanyl, 2- or 3-thienyl,
  wherein the phenyl, biphenyl, naphthyl, pyridyl, furanyl or thienyl rings may be independently optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-allyl)$_2$, SO$_2$—CH$_3$, COOH, COO—(C$_1$–C$_6$)-alkyl or CONH$_2$;

1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;

R2 is selected from the group consisting of H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)n-furyl, C(O)-(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl and C(O)—(CH$_2$) $_n$-furyl,
  where n is 0–5 and wherein the phenyl, thienyl, pyridyl or furyl ring may be independently optionally substituted up to two times by Cl, F, CN, CF$_3$, (C$_1$–C$_3$)-alkyl, OH or O—(C$_1$–C$_6$)-alkyl;

R3 is selected from the group consisting of H, (C$_1$–C$_6$)-alkyl, F, CN, N$_3$, O—(C$_1$–C$_6$)-alkyl, (CH$_2$)$_n$-phenyl, (CH$_2$)$_n$-thienyl, (CH$_2$)$_n$-pyridyl, (CH$_2$)$_n$-furyl, where n is 0–5 and wherein the phenyl, thienyl, pyridyl or furyl ring may be independently optionally substituted up to two times by Cl, F, CN, $CF_3$, $(C_1-C_3)$-alkyl, OH or O—$(C_1-C_6)$-alkyl;

$(C_2-C_6)$-alkynyl, $(C_2-C_6)$-alkenyl, $C(O)OCH_3$, $C(O)OCH_2CH_3$, $C(O)OH$, $C(O)NH_2$, $C(O)NHCH_3$, $C(O)N(CH_3)_2$ and $OC(O)CH_3$;

R4 is selected from the group consisting of $(C_8-C_6)$-cycloalkyl, wherein one or more hydrogens of the alkyl radicals may be optionally replaced by fluorine, or a hydrogen may be optionally replaced by OH, $OC(O)CH_3$, $OC(O)H$, $O-CH_2-Ph$ or $O-(C_1-C_4)$-alkyl;

$(CH_2)_n$—A—R8, where n is 1–6, except for when $(CH_2)_n$—A—R8 is —$CH_2$—O—$CH_2$-phenyl, then the phenyl is unsubstituted; and $(CH_2)_r$—B—R9, where r is 1–6;

A is selected from the group consisting of O, S, SO and $SO_2$;

B is selected from the group consisting of NH, N—$(C_1-C_6)$-alkyl, NCHO and N(CO—$CH_3$);

R8 is selected from the group consisting of $(C_5-C_{24})$-alkyl, $(C_3-C_{10})$-cycloalkyl, wherein one or more hydrogens of the alkyl radicals may be optionally replaced by fluorine, or a hydrogen may be optionally replaced by OH, $OC(O)CH_3$, $OC(O)H$, $O-CH_2-Ph$ or $O-(C_1-C_4)$-alkyl; and $(CH_2)_m$-aryl, where m is 0–6 and aryl is selected from the group consisting of phenyl, naphthyl, biphenyl, thienyl and pyridyl, wherein the aryl moiety may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $SO_2$—$NH_2$, $SO_2$—NH$(C_1-C_8$-alkyl), $SO_2$—N$(C_1C_8$-alkyl$)_2$, $SO_2$—NH$(C_3-C_8$-cycloalkyl), $SO_2$-N$(C_3-C_8$-cycloalkyl$)_2$, $(CH_2)_m$—$SO_2$—$NH_2$, $(CH_2)_m$—$SO_2$—NH—$(C_1-C_6)$-alkyl, $(CH_2)_{m-SO2}$—N$((C_1-C_6)$-alkyl$)_2$, where m is 1–6, $SO_2$—N(=CH—N$(CH_3)_2$), $(C_1-C_6)$-alkyl, $(C_3-C_6)$-cycloalkyl, COOH, COO$(C_1-C_6)$alkyl, COO$(C_3-C_6)$cycloalkyl, $CONH_2$, CONH$(C_1-C_6)$alkyl, CON$[(C_1-C_6)$alkyl$]_2$, CONH$(C_3-C_6)$cycloalkyl, $NH_2$, NH$(C_1-C_6)$-alkyl, N$(C_1-C_6$-alkyl$)_2$, NH—CO—$(C_1-C_6)$-alkyl, NH—CO—phenyl, NH—$SO_2$—$(C_1-C_8$-alkyl), N$(C_1-C_6$-alkyl)—$SO_2$—$(C_1-C_8$-alkyl), NH—$SO_2$-phenyl, wherein the phenyl ring may be optionally substituted up to two times by F, Cl, CN, OH, $(C_1-C_6)$-alkyl, O—$(C_1-C_6)$-alkyl, $CF_3$, COOH, COO$(C_1-C_6)$-alkyl or $CONH_2$;

pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, where p is 0–3;

R9 is $(CH_2)_m$-aryl, where m can be 0–6 and aryl is selected from the group consisting of phenyl, naphthyl, biphenyl, thienyl and pyridyl, wherein the aryl moiety may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $SO_2$—$NH_2$, $SO_2$—NH$(C_1-C_8$-alkyl), $SO_2$—N$(C_1-C_8$-alkyl$)_2$, $SO_2$—NH$(C_3-C_8$-cycloalkyl), $SO_2$—N$(C_3-C_8$-cycloalkyl$)_2$, $(CH_2)_m$—$SO_2$—$NH_2$, $(CH_2)_m$—$SO_2$—NH—$(C_1-C_6)$-alkyl, $(CH_2)_m$—$SO_2$—N$((C_1-C_6)$-alkyl$)_2$, where m is 1–6, $SO_2$—N (=CH—N$(CH_3)_2$), $(C_1-C_6)$-alkyl, $(C_3-C_6)$-cycloalkyl, COOH, COO$(C_1-C_6)$alkyl, COO$(C_3-C_6)$cycloalkyl, $CONH_2$, CONH$(C_1-C_6)$alkyl, CON$[(C_1-C_6)$alkyl$]_2$, CONH$(C_3-C_6)$cycloalkyl, $NH_2$, NH$(C_1-C_6)$-alkyl, N$(C_1-C_6$-alkyl$)_2$, NH—CO—$(C_1-C_6)$-alkyl, NH—CO—phenyl, NH—$SO_2$—$(C_1-C_8$-alkyl), N$(C_1-C_6$-alkyl)—$SO_2$—$(C_1-C_8$-alkyl), NH—$SO_2$-phenyl, wherein the phenyl ring may be optionally substituted up to two times by F, Cl, CN, OH, $(C_1-C_6)$-alkyl, O—$(C_1-C_6)$-alkyl, $CF_3$, COOH, COO$(C_1-C_6)$-alkyl or $CONH_2$;

pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, where p is 0–3;

and a physiologically acceptable salt thereof.

In a particularly preferred embodiment, compounds of the formula I are contemplated wherein:

Y is a direct bond;

x is $CH_2$;

R1, R1' are independently selected from the group consisting of H, F, Cl, Br, I, $CF_3$, $NO_2$, CN, COOH, COO$(C_1-C_6)$alkyl, $CONH_2$, CONH$(C_1-C_6)$alkyl, CON$[(C_1-C_6)$alkyl$]_2$, $(C_1-C_6)$-alkyl, $(C_2-C_6)$-alkenyl, $(C_2-C_6)$-alkynyl, O—$(C_1-C_6)$-alkyl, wherein one or more hydrogens of the alkyl radicals may be optionally replaced by fluorine, or a hydrogen may be optionally replaced by OH, $OC(O)CH_3$, $OC(O)H$, $O-CH_2-Ph$, $NH_2$, NH—CO—$CH_3$ or N(COOCH$_2$Ph)$_2$;

$SO_2$—$NH_2$, $SO_2$NH$(C_1-C_6)$-alkyl, $SO_2$N$[(C_1-C_6)$-alkyl]$_2$, S—$(C_1C_6)$-alkyl, S—$(CH_2)_n$-phenyl, SO—$(C_1-C_6)$-alkyl, SO—$(CH_2)_n$-phenyl, $SO_2$-$(C_1-C_6)$-alkyl, $SO_2$—$(CH_2)_n$-phenyl, where n is 0–6 and wherein the phenyl radical is optionally substituted up to two times by F, Cl, Br, OH, $CF_3$, $NO_2$, CN, $OCF_3$, O—$(C_1-C_6)$-alkyl, $(C_1-C_6)$-alkyl or $NH_2$;

$NH_2$, NH—$(C_1-C_6)$-alkyl, N$((C_1-C_6)$-alkyl$)_2$, NH$(C_1-C_7)$-acyl, phenyl, biphenyl, O—$(CH_2)_n$-phenyl, where n can be 0–6, 1- or 2-naphthyl, 2-, 3- or 4-pyridyl, 2- or 3-furanyl, 2- or 3-thienyl, wherein the phenyl, biphenyl, naphthyl, pyridyl, furanyl or thienyl rings may be independently optionally substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-allyl, N$((C_1-C_6)$-alkyl$)_2$, $SO_2$—$CH_3$, COOH, COO—$(C_1-C_6)$-alkyl, $CONH_2$;

1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;

R2 is selected from the group consisting of H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, $C(O)$—$(C_1-C_6)$-alkyl, $C(O)$—$(C_3-C_6)$-cycloalkyl, $C(O)$—$(CH_2)_n$-phenyl, $C(O)$—$(CH_2)_n$-thienyl, $C(O)$—$(CH_2)_n$-pyridyl and $C(O)$—$(CH_2)_n$-furyl, where n is 0–5, and wherein the phenyl, thienyl, pyridyl or furyl ring may be independently optionally substituted up to two times by Cl, F, CN, $CF_3$, $(C_1-C_3)$-alkyl, OH, O—$(C_1-C_6)$-alkyl;

R3 is selected from the group consisting of H and F;
R4 is selected from the group consisting of ($C_8$–$C_{16}$)-cycloalkyl,
  wherein one or more hydrogens of the alkyl radicals may be optionally replaced by fluorine,
  or a hydrogen may be optionally replaced by OH, OC(O)CH$_3$, OC(O)H, O—CH$_2$—Ph or O—($C_1$–$C_4$)-alkyl;
($CH_2$)$_n$—A—R8, where n is 1–6, except for when ($CH_2$)$_n$—A—R8 is —CH$_2$—O—CH$_2$-phenyl, then the phenyl is unsubstituted; and
($CH_2$)$_r$—B—R9, where r is 1–6;
A is selected from the group consisting of O and S;
B is selected from the group consisting of NH, N—($C_1$–$C_6$)-alkyl, NCHO and N(CO—CH$_3$);
R8 is selected from the group consisting of ($C_5$–$C_{24}$)-alkyl, ($C_3$–$C_{10}$)-cycloalkyl,
  wherein one or more hydrogens of the alkyl radicals may be optionally replaced by fluorine,
  or a hydrogen may be optionally replaced by OH, OC(O)CH$_3$, OC(O)H, O—CH$_2$—Ph or O—($C_1$–$C_4$)-alkyl; and
($CH_2$)$_m$-aryl, where m is 0–6 and aryl is selected from the group consisting of phenyl, naphthyl, biphenyl, thienyl and pyridyl;
  wherein the aryl moiety may be optionally substituted up to two times by F, Cl, Br, OH, CF$_3$, NO$_2$, CN, OCF$_3$, O—($C_1$–$C_6$)-alkyl, S—($C_1$–$C_6$)-alkyl, SO—($C_1$–$C_6$)-alkyl, SO$_2$—($C_1$–$C_6$)-alkyl, SO$_2$—NH$_2$, SO$_2$—NH($C_1$–$C_8$-alkyl), SO$_2$—N($C_1$–$C_8$-alkyl)$_2$, SO$_2$—NH($C_3$–$C_8$-cycloalkyl), SO$_2$—N($C_3$–$C_5$-cycloalkyl)$_2$, (CH$_2$)$_m$—SO$_2$—NH$_2$, (CH$_2$)$_m$—SO$_2$—NH—($C_1$–$C_6$)-alkyl, (CH$_2$)$_m$—SO$_2$—N(($C_1$–$C_6$)-alkyl)$_2$, where m is 1–6, SO$_2$—N(=CH—N (CH$_3$)$_2$), ($C_1$–$C_6$)-alkyl, ($C_3$–$C_6$)-cycloalkyl, COOH, COO($C_1$–$C_6$)alkyl, COO($C_3$–$C_6$)cycloalkyl, CONH$_2$, CONH($C_1$–$C_6$)alkyl, CON[($C_1$–$C_6$)alkyl]$_2$, CONH($C_3$–$C_6$)cycloalkyl, NH$_2$, NH($C_1$–$C_6$)-alkyl, N($C_1$–$C_6$-alkyl)$_2$, NH—CO—($C_1$–$C_6$)-alkyl, NH—CO—phenyl, NH—SO$_2$—($C_1$–$C_8$-alkyl), N($C_1$–$C_6$-alkyl)—SO$_2$—($C_1$–$C_8$-alkyl), NH—SO$_2$-phenyl,
    wherein the phenyl ring may be optionally substituted up to two times by F, Cl, CN, OH, ($C_1$–$C_6$)-alkyl, O—($C_1$–$C_6$)-alkyl, CF$_3$, COOH, COO($C_1$–$C_6$)-alkyl or CONH$_2$;
  pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;
R9 is (CH$_2$)$_m$-aryl, where m is 0–6 and aryl is selected from the group consisting of phenyl, naphthyl, biphenyl, thienyl and pyridyl;
  wherein the aryl moiety may be optionally substituted up to two times by F, Cl, Br, OH, CF$_3$, NO$_2$, CN, OCF$_3$, O—($C_1$–$C_6$)-alkyl, S—($C_1$–$C_6$)-alkyl, SO—($C_1$–$C_6$)-alkyl, SO$_2$—($C_1$–$C_6$)-alkyl, SO$_2$—NH$_2$, SO$_2$—NH($C_1$–$C_5$-alkyl), SO$_2$—N($C_1$–$C_8$-alkyl)$_2$, SO$_2$—NH($C_3$–$C_8$-cycloalkyl), SO$_2$—N($C_3$–$C_8$-cycloalkyl)$_2$, (CH$_2$)$_m$—SO$_2$—NH$_2$, (CH$_2$)$_m$—SO$_2$—NH—($C_1$–$C_6$)-alkyl, (CH$_2$)$_m$—SO$_2$—N(($C_1$–$C_6$)-alkyl)$_2$, where m can be 1–6, SO$_2$—N(=CH—N (CH$_3$)$_2$), ($C_1$–$C_6$)-alkyl, ($C_3$–$C_6$)-cycloalkyl, COOH, COO($C_1$–$C_6$)alkyl, COO($C_3$–$C_6$)cycloalkyl, CONH$_2$, CONH($C_1$–$C_6$)alkyl, CON[($C_1$–$C_6$)alkyl]$_2$, CONH($C_3$–$C_6$)cycloalkyl, NH$_2$, NH($C_1$–$C_6$)-alkyl, N($C_1$–$C_6$-alkyl)$_2$, NH—CO—($C_1$–$C_6$)-alkyl, NH—CO—phenyl, NH—SO$_2$—($C_1$–$C_8$-alkyl), N($C_1$–$C_6$-alkyl)—SO$_2$—($C_1$–$C_8$-alkyl), NH—SO$_2$-phenyl,
    wherein the phenyl ring may be optionally substituted up to two times by F, Cl, CN, OH, ($C_1$–$C_6$)-alkyl, O—($C_1$–$C_6$)-alkyl, CF$_3$, COOH, COO($C_1$–$C_6$)-alkyl or CONH$_2$;
  pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;
and a physiologically acceptable salt thereof.

Another preferred embodiment of the invention is directed to compounds of the formula I wherein:
Y is a direct bond;
x is CH$_2$;
R1, R1' are independently selected from the group consisting of H, F, Cl, Br, I and ($C_1$–$C_6$)-alkyl;
R2 is selected from the group consisting of H and ($C_1$–$C_6$)-alkyl;
R3 is selected from the group consisting of H and F;
R4 is selected from the group consisting of ($C_8$–$C_6$)-cycloalkyl and (CH$_2$)$_n$—A—R8, where n is 1–6, except when (CH$_2$)$_n$—A—R8 is —CH$_2$—O—CH$_2$-phenyl, then the phenyl is unsubstituted;
A is selected from the group consisting of O and S;
R8 is selected from the group consisting of ($C_5$–$C_{24}$)-alkyl and (CH$_2$)$_m$-aryl, where m is 0–6 and aryl is phenyl;
  wherein the aryl moiety may be optionally substituted up to two times by F, Cl, Br, OH, CF$_3$, NO$_2$, CN, OCF$_3$, O—($C_1$–$C_6$)-alkyl, S—($C_1$–$C_6$)-alkyl, SO—($C_1$–$C_6$)-alkyl, SO$_2$—($C_1$–$C_6$)-alkyl, SO$_2$—NH$_2$, SO$_2$—NH($C_1$–$C_8$-alkyl), SO$_2$—N($C_1$–$C_8$-alkyl)$_2$, SO$_2$—NH($C_3$–$C_8$-cycloalkyl), SO$_2$—N($C_3$–$C_8$-cycloalkyl)$_2$, (CH$_2$)$_m$—SO$_2$—NH$_2$, (CH$_2$)$_m$—SO$_2$—NH—($C_1$–$C_6$)-alkyl, (CH$_2$)$_m$—SO$_2$—N(($C_1$–$C_6$)-alkyl)$_2$, where m is 1–6, SO$_2$—N(=CH—N (CH$_3$)$_2$), ($C_1$–$C_6$)-alkyl, ($C_3$–$C_6$)-cycloalkyl, COOH, COO($C_1$–$C_6$)alkyl, COO($C_3$–$C_6$)cycloalkyl, CONH$_2$, CONH($C_1$–$C_6$)alkyl, CON[($C_1$–$C_6$)alkyl]$_2$, CONH($C_3$–$C_6$)cycloalkyl, NH$_2$, NH($C_1$–$C_6$)-alkyl, N($C_1$–$C_6$-alkyl)$_2$, NH—CO—($C_1$–$C_6$)-alkyl, NH—CO—phenyl, NH—SO$_2$—($C_1$–$C_8$-alkyl), N($C_1$–$C_6$-alkyl)—SO$_2$—($C_1$–$C_6$-alkyl), NH—SO$_2$-phenyl,
    wherein the phenyl ring may be optionally substituted up to two times by F, Cl, CN, OH, ($C_1$–$C_6$)-alkyl, O—($C_1$–$C_6$)-alkyl, CF$_3$, COOH, COO($C_1$–$C_6$)-alkyl or CONH$_2$;
  pyrrolidin-l-yl, morpholin-1-yl, piperidin-l-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;
and a physiologically acceptable salt thereof.

The invention relates to compounds of the formula I, in the form of their racemates, racemic mixtures and pure enantiomers, and to their diastereomers and mixtures thereof.

The alkyl, alkenyl and alkynyl radicals in the substituents R1, R1', R2, R3, R4, R8 and A can be either straight-chain or branched.

Pharmaceutically acceptable salts are particularly suitable for medicinal applications compared with the starting or base compounds because of their higher solubility in water. These typically salts have a pharmaceutically tolerable anion or cation. Suitable pharmaceutically acceptable acid addition salts of the compounds of formula I according to the invention are salts of inorganic acids, such as hydrochloric acid, hydrobromic, phosphoric, metaphosphoric, nitric, sulfonic and sulfuric acid and organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. For medicinal purposes, the chlorine salt is particularly preferably used. Suitable pharmaceutically acceptable basic salts are ammonium salts, alkali metal salts (such as sodium and potassium salts) and alkaline earth metal salts (such as magnesium and calcium salts).

Salts with a non-pharmaceutically acceptable anion are also included within the scope of the invention as useful intermediates for the production or purification of pharmaceutically acceptable salts and/or for use in non-therapeutic, for example in-vitro, applications.

The expression "physiologically functional derivative" used herein relates to any physiologically acceptable derivative of a compound of the formula I according to the invention, e.g. an ester, which on administration to a mammal, for example, man, is able (directly or indirectly) to form a compound of the formula I or an active metabolite thereof.

The physiologically functional derivatives also include prodrugs of the compounds according to the invention. Such prodrugs can be metabolized in vivo to a compound according to the invention. These prodrugs can themselves be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) according to formula (I)" refer to compound(s) of the formula (I) as described above, and their salts, solvates and physiologically functional derivatives as described herein.

The compounds of formula (I) are useful in the treatment of type II diabetes and in the treatment of obesity. Treatment includes either the prophylaxis or the amelioration of the disorder. In order to achieve the treatment, an effective amount of a compound of formula (I) is administered to a patient in need thereof. An "effective amount" is the amount which achieves the treatment of the specified state.

The effective amount of a compound according to formula (I) which is necessary in order to achieve the desired biological effect is dependent on a number of factors, e.g. the specific compound selected, the intended use, the manner of administration and the clinical condition of the patient. In general, the daily dose is in the range from 0.3 mg to 100 mg (typically from 3 mg to 50 mg) per day per kilogram of body weight, e.g. 3–10 mg/kg/day. An intravenous dose can be, for example, in the range from 0.3 mg to 1.0 mg/kg, which can be suitably administered as an infusion of 10 ng to 100 ng per kilogram per minute. Suitable infusion solutions for these purposes may contain, for example, from 0.1 ng to 10 mg, typically from 1 ng to 10 mg per milliliter. Individual doses can contain, for example, from 1 mg to 10 g of the active compound. Thus, ampoules for injections can contain, for example, from 1 to 100 mg and orally administrable individual dose formulations, such as, for example, tablets or capsules, may contain, for example, from 1.0 to 1000 mg, typically from 10 to 600 mg. In the case of pharmaceutically tolerable salts, the abovementioned weight details relate to the weight of the dihydrothiazolium ion derived from the salt. For the prophylaxis or therapy of the abovementioned conditions, the compounds according to formula (I) itself may be used as the compound, but they are preferably present in the form of a pharmaceutical composition with an acceptable vehicle. The vehicle must of course be acceptable, in the sense that it is compatible with the other constituents of the composition and is not harmful to the patient's health. The vehicle may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions according to the invention can be prepared by one of the known pharmaceutical methods, which essentially consist in mixing the constituents with pharmacologically tolerable excipients and/or auxiliaries.

Pharmaceutical compositions according to the invention are those which are suitable for oral, rectal, topical, peroral (e.g. sublingual) and parenteral (e.g. subcutaneous, intramuscular, intradermal or intravenous) administration, although the most suitable manner of administration in each individual case is dependent on the nature and severity of the condition to be treated and on the identity of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxy-propylmethylcellulose phthalate and anionic polymers of methacrylic acid and methyl methacrylate.

Suitable pharmaceutical compounds of formula (I) for oral administration may be present in separate units, such as, for example, capsules, cachets, lozenges or tablets which in each case contain a certain amount of the compound according to formula (I); as powder or granules; as a solution or suspension in an aqueous or nonaqueous liquid; or as an oil-in-water or water-in-oil emulsion. As already mentioned, these compositions may be prepared by any suitable pharmaceutical method which includes contacting the active compound with the pharmaceutically acceptable vehicle (which can consist of one or more additional constituents). In general, the compositions are prepared by uniform and homogeneous mixing of the active compound with a liquid and/or finely divided solid vehicle, after which the product, if necessary, is shaped. Thus a tablet, for example, may be prepared by pressing or shaping a powder or granules of the compound, and if desired, with one or more additional constituents. Pressed tablets may be prepared by tabletting the compound in free-flowing form, for example, a powder or granules, and if desired, mixed with a binder, lubricant, inert diluent and/or one (a number of) surface-active/dispersing agents in a suitable machine. Shaped tablets may be prepared by shaping the pulverulent compound, moistened with an inert liquid diluent, in a suitable machine.

Pharmaceutical compositions which are suitable for peroral (sublingual) administration include but are not limited to lozenges which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations comprising a compound according to formula (I), which are preferably isotonic with the blood of the intended recipient. These preparations are preferably administered intravenously although the administration may also take place subcutaneously, intramuscularly or intradermally as an injection. These preparations may preferably be prepared by mixing the compound with water and rendering the obtained solution sterile and isotonic with the blood. Injectable compositions according to the invention in general contain from 0.1 to 5 % by weight of the active compound.

Suitable pharmaceutical compositions for rectal administration are preferably present as individual dose suppositories. These may be prepared by mixing a compound according to formula (I) with one or more conventional solid vehicles, for example cocoa butter, and shaping the resulting mixture.

Suitable pharmaceutical compositions for topical application to the skin are preferably present as an ointment, cream, lotion, paste, spray, aerosol or oil. Vehicles which may be used are, for example, petroleum jelly, lanolin, polyethylene glycols and alcohols as well as combinations of two or more of these substances. The active compound is in general present in a concentration of 0.1 to 15 % by weight of the composition, for example of 0.5 to 2 %.

Transdermal administration of the active compounds of formula (I) is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is about 1 % to 35 %, preferably about 3 % to 15 %. As a particular possibility, the active compound may be released by electrotransport or iontophoresis, as described, for example, in Pharmaceutical Research, 2(6): 318 (1986).

In addition, the invention relates to a process for the preparation of the compounds of the formula I, which comprises obtaining the compounds of the formula I by the following reaction scheme:

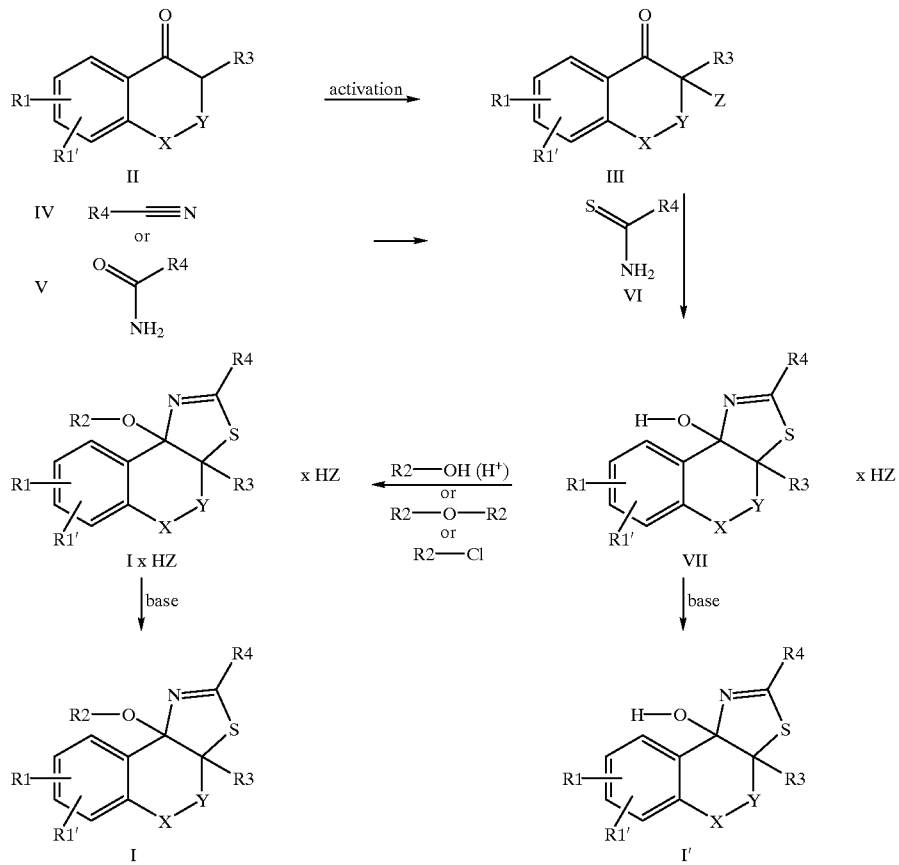

For this synthesis, compounds of formula II

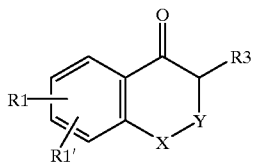

Formula II in which R1, R1', R3 and X and Y have the meaning indicated above, are activated and converted into compounds of formula III, in which Z is the radical of an activated ester of an inorganic or organic acid.

The compounds of formula III are reacted further with thioamides of the formula VI

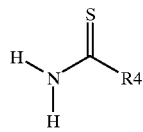

in which R4 has the meaning indicated above, to yield compounds of formula VII or I', where, if desired, the compounds of the formula I' are converted into their acid addition salts of the formula VII using organic or inorganic acids or salts of the formula VII obtained are converted into the free basic compounds of the formula I' using organic or inorganic bases.

Suitable inorganic acids include but are not limited to, for example: hydrohalic acids such as hydrochloric acid and hydrobromic acid, as well as sulfuric acid, phosphoric acid and amidosulfonic acid.

Organic acids which may be used include but are not limited to, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazine-4(3H)-one-2,2-dioxide.

The procedure described above is preferably carried out so that the compounds of formula III are reacted with the thioamides of formula VI in the molar ratio from 1:1 to 1:1.5. The reaction is preferably carried out in an inert solvent, e.g. in polar organic solvents such as dimethylformamide, dimethylacetamide, N-methyl-2-pyrrolidone, dioxane, tetrahydrofuran, acetonitrile, nitromethane or diethylene glycol dimethyl ether. Particularly preferred solvents, include, for example, methyl acetate and ethyl acetate, short-chain alcohols such as methanol, ethanol, propanol, isopropanol, and lower dialkyl ketones, such as, for example, acetone, butan-2-one or hexan-2-one. Mixtures of the reaction media mentioned may also be used; and mixtures of the solvents mentioned may also be used with solvents which taken per se are less suitable, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, where the more polar solvent in each case is preferably used in excess. The reaction components may be suspended or dissolved in the respective reaction medium. However, it is noted that the reaction components may also be reacted without solvent, for example when the thioamide used has a very low melting point. Thus, the reaction proceeds in an only slightly exothermic manner and may be carried out between −10° C. and 150° C., preferably between 30° C. and 100° C. A temperature range between 50° C. and 90° C. proves to be particularly favorable.

The reaction time is largely dependent on the reaction temperature and is preferably between 2 minutes and 3 days at relatively high and relatively low temperatures, respectively. In the preferable temperature range, the reaction time is in general between 5 minutes and 48 hours.

Frequently, the compounds of formula (VII) separate in the form of their poorly soluble acid addition salts in the course of the reaction, necessitating that a suitable precipitating agent be added when needed. The precipitating agents used are, for example, hydrocarbons such as benzene, toluene, cyclohexane or heptane or tetrachloromethane; in particular, alkyl acetates such as ethyl acetate or n-butyl acetate or dialkyl ethers such as diethyl ether, diisopropyl ether, di-n-butyl ether or tert-butyl methyl ether prove particularly suitable. If the reaction mixture remains in solution after the end of the reaction, the salts of the compounds (VII) may be precipitated using one of the precipitating agents mentioned, if desired after concentration of the reaction solution. Furthermore, the solution of the reaction mixture may also be preferably filtered into the solution of one of the precipitating agents mentioned with stirring. Since the reaction of the compounds of formula (III) with the thioamides of formula (VI) proceeds virtually quantitatively, the crude products obtained are typically already analytically pure. Work-up of the reaction mixture may also be carried out such that the reaction mixture is rendered alkaline with addition of an organic base, for example, triethylamine or diisobutylamine or ammonia or morpholine or piperidine or 1,8-diazabicyclo[5.4.0]undec-7-ene, and the crude reaction product is purified chromatographically, e.g. on a silica gel column, after concentration. Suitable elution media are preferably, for example, mixtures of ethyl acetate with methanol, mixtures of dichloromethane with methanol, mixtures of toluene with methanol or ethyl acetate or mixtures of ethyl acetate with hydrocarbons such as heptane. If the purification of the crude product is carried out in the manner last described, an acid addition product of the formula (VII) may be obtained from the pure base of the formula I' thus obtained by dissolving or suspending the base in an organic protic solvent such as methanol, ethanol, propanol or isopropanol or in an organic aprotic solvent such as ethyl acetate, diethyl ether, diisopropyl ether, tert-butyl methyl ether, dioxane, tetrahydrofuran, acetone or butan-2-one and then treating this mixture with an at least equimolar amount of an inorganic acid such as, for example, hydrochloric acid, dissolved in an inert solvent, for example, diethyl ether or ethanol, or another of the inorganic or organic acids mentioned further above.

The compounds of the formula I' may be recrystallized from an inert, suitable solvent, for example, acetone, butan-2-one, acetonitrile, nitromethane. Particularly preferred, however, is reprecipitation from a solvent, for example, dimethylformamide, dimethylacetamide, nitromethane, acetonitrile, most preferably methanol or ethanol.

The reaction of the compounds of the formula II with the thioamides of the formula (VI) may also be carried out such that at least an equimolar amount of a base, for example, triethylamine, is added to the reaction mixture and the compounds of formula (I') thus obtained are then optionally converted into their acid addition products of formula (VII).

A possible radical of an activated ester Z in the compounds of the formula (III) is, for example: Cl, Br, I, O—C(O)—($C_6H_4$)-4-$NO_2$, O—$SO_2$—$CH_3$, O—$SO_2$—$CF_3$, O—$SO_2$—($C_6H_4$)-4-$CH_3$, O—$SO_2$-$C_6H_4$.

The acid addition products of formula (VII) and (I)×HZ may be reacted to give the compounds of the formulae (I) and (I') by treatment with bases. Possible bases are, for example, solutions of inorganic hydroxides, such as lithium, sodium, potassium, calcium or barium hydroxide, carbonates or hydrogencarbonates, such as sodium or potassium carbonate, sodium or potassium hydrogencarbonate, ammonia and amines, such as triethylamine, diisopropylamine, dicyclohexylamine, piperidine, morpholine, methyldicyclohexylamine.

Thioamides of the formula (VI) are either commercially obtainable or can be obtained, for example, by reaction of the corresponding carboxamide of formula (V) with phosphorus pentasulfide in pyridine (R. N. Hurd, G. Delameter, Chem. Rev. 61, 45 (1961)), or with Lawesson's reagent in toluene, pyridine, hexamethylphosphoric triamide (Scheibye, Pedersen und Lawesson: Bull. Soc. Chim. Belges 87, 229 (1978)), preferably in a mixture of tetrahydrofuran with 1,3-dimethyl-3,4,5,6-tetrahydro-2(1H)-pyrimidinone or 1,3-dimethyl-2-imidazolidinone. Hydroxyl, amino or additional carbonyl functions are in this case preferably protected using a removable protective function, such as, for example, a benzyl, tert-butyloxycarbonyl or benzyloxycarbonyl radical or converted into an optionally cyclic acetal. Methods for the protection reaction are described, for example, in Th. W. Greene and P. G. M. Wuts, Protective Groups in Organic Synthesis, Second Edition, 1991, John Wiley & Sons, New York.

Thioamides of formula (VI) are also prepared by reacting nitrites of the formula IV

Formula IV with hydrogen sulfide (see, for example, Houben-Weyl IX, 762) or thioacetamide (see, for example, E. C. Taylor, J. A. Zoltewicz, J. Am. Chem. Soc. 82, 2656 (1960)) or O,O-diethyl-dithiophosphoric acid. The reactions with hydrogen sulfide are preferably carried out in an organic solvent, such as, methanol or ethanol, those with thioacetamide in a solvent, such as, dimethylformamide with addition of hydrochloric acid, and those with O, O-diethyldithiophosphoric acid in a solvent such as ethyl acetate under acidic, e.g. HCl, conditions at room temperature or with warming.

The examples listed below serve to illustrate the invention, but without restricting it. The measured melting or decomposition points (m.p.) were not corrected and are generally dependent on the heating rate.

The compounds of the formula I exhibit favorable effects on liquid metabolism in particular, they have been found to be suitable as anorectics. The compounds may be employed on their own or in combination with further anorectics. Examples include, but are not limited to, DECORPA© (from Pierre Fabre Pharma Common name, sterculia), XENICAL© (from Roche, common name orlistat), ANTIADIPOSITUM X-112S (from Haeseler, common name, D-norpseudoephedrin-HCl), FASUPOND© (from Eu Rho Arzneil, common name, D-norseudoephedrin-HCl), MIRAPRONT© (from Mack, Illert., common name, D-norpseudoephedrin-Poly(styrol, divinylbenzol) sulfonate), REGENON© l-retard (from Temmler Pharma, common name, Amfepramon-HCl), RONDIMEN© (from ASTA Medica AWD, common name, Mefenorex-HCl), TENUATE© Retard (from Artegodan, common name, Amfepramon-HCl), VITA-SCHLANKTROPFEN SCHUCK (from Schuck, common name, D-norpseudoephedrin-HCl), VENCIPON© N (from Artesan, common name, Ephedrin-HCl), CEFAMADAR© (from Cefak, common name Madar D4), and HELIANTHUS TUBEROSUS (Plantina). The compounds are suitable for the prophylaxis and, in particular, for the treatment of obesity. In addition, the compounds are suitable for the prophylaxis and, in particular, for the treatment of type II diabetes.

The activity of the compounds has been tested as follows:
Biological test model:
The anorectic action was tested on male or female NMRI mice. After withdrawal of feed for 24 hours, the test preparation was administered via a stomach tube. Kept individually and with free access to drinking water, the animals were offered evaporated milk 30 minutes after giving the preparation. The consumption of evaporated milk was determined half-hourly for 7 hours and the general condition of the animals was observed. The measured milk consumption was compared with that of the untreated control animals.

TABLE 1

Examples

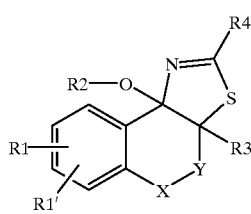

Formula I

| Example | R1; R1' | R2 | R3 | R4 | Y | X | Salt | m.p. [° C.] |
|---|---|---|---|---|---|---|---|---|
| 1 | 6-Cl; H | H | H | $CH_2$—O-phenyl | — | $CH_2$ | — | 121 |
| 2 | 6-Cl; H | H | H | $CH_2$—O—($C_6H_4$-4-$OCH_3$) | — | $CH_2$ | — | 110 |
| 3 | 6-Cl; H | H | H | $CH_2$—O—($C_6H_4$-2-Cl) | — | $CH_2$ | — | 178 |
| 4 | 6-Cl; H | H | H | $CH_2$—O—($C_6H_4$-3-Cl) | — | $CH_2$ | — | 121 |
| 5 | 6-Cl; H | H | H | $CH_2$—O—($C_6H_4$-4-Cl) | — | $CH_2$ | — | 123 |
| 6 | 6-Cl; H | H | H | $CH_2$—O-phenyl-2,4-di-Cl | — | $CH_2$ | HBr | 170 |
| 7 | 6-Cl; H | H | H | adamant-1-yl | — | $CH_2$ | — | 173 |
| 8 | 6-Cl; H | H | H | $CH_2$—O-(phenyl-3,5-di-Cl) | — | $CH_2$ | — | 125 |
| 9 | 6-Cl; H | H | H | $CH_2$—O-(phenyl-4-tBu) | — | $CH_2$ | — | 123 |
| 10 | 6-Cl; H | H | H | $CH_2$—O—$CH_2$—$CH_2$—$C_6H_5$ | — | $CH_2$ | — | 94 |
| 11 | 6-Cl; H | H | H | $CH_2$—O—$(CH_2)_5$—$CH_3$ | — | $CH_2$ | — | 78 |
| 12 | 6-Cl; H | H | H | $CH_2$—S—$CH_2$—$C_6H_5$ | — | $CH_2$ | — | 102 |

TABLE 2

Anorectic action, measured as the reduction of the cumulated milk consumption of treated animals in comparison to that of untreated animals.

Compound/Example

Formula I

| | Oral dose [mg/kg] | Number of animals/ cumulated milk consumption of the treated animals (male) N/[ml] | Number of animals/ cumulated milk consumption of the untreated control animals (male) N/[ml] | Reduction of the cumulated milk consumption in % of the control |
|---|---|---|---|---|
| Example 1 | 50 | 5/0.42 | 5/2.90 | 86 |
| Example 2 | 50 | 5/0.34 | 5/2.90 | 88 |
| Example 3 | 50 | 5/0.78 | 5/2.90 | 73 |
| Example 5 | 50 | 5/0.42 | 5/4.18 | 90 |
| Example 6 | 50 | 5/0.22 | 5/4.20 | 95 |
| Example 8 | 50 | 5/0.28 | 5/4.20 | 93 |
| Example 9 | 50 | 5/0.26 | 5/3.46 | 93 |
| Example 10 | 50 | 5/1.04 | 5/4.64 | 78 |
| Example 11 | 50 | 5/1.34 | 5/4.64 | 71 |
| Example 12 | 50 | 5/1.36 | 5/4.64 | 71 |

The data from Table 2 is indicates that the compounds of the formula I exhibit very good anorectic action.

The preparation of some examples is described in detail below; the other compounds of the formula I were obtained by a similar procedure and would be well within the purview of the skilled artisan:

PREPARATION EXAMPLE 1

EXAMPLE 1 (Compound 1)

Synthesis of 6-chloro-2-phenoxymethyl-8,8a-dihydroindeno[1,2-d]thiazol-3a-ol a) 2-bromo-5-chloroindan-1-on:

At room temperature, 10 g (0.06 Mol) of 5-chloroindan-1-one were dissolved with stirring in 120 ml of glacial acetic acid. 0.05 ml of a 48 % strength solution of HBr in water and then 3.074 ml (0.06 mol) of bromine, dissolved in 25 ml of glacial acetic acid, was added dropwise. After 2 h of stirring at room temperature, the reaction was stopped (monitored by TLC). The solution of the crude product was slowly added dropwise, with stirring, to 300 ml of ice-water. The precipitated crude product was filtered off with suction and washed thoroughly with water. The moist residue was removed from the filter using ethyl acetate, and the phases of the filtrate were separated. The organic phase was dried over sodium sulfate, filtered and concentrated under reduced pressure. The residue was dissolved in 120 ml of hot n-heptane; the hot solution was filtered through a pleated filter and the solution was then left to crystallize at 0° C. The crystalline product was filtered off with suction and dried under reduced pressure. The crystalline product has a melting point of 94–96° C.

b) 6-chloro-2-phenoxymethyl-8,8a-dihydroindeno[1,2-d]thiazol-3a-ol:

At room temperature, 0.49 g of 2-bromo-5-chloroindan-1-on were dissolved in 10 ml of dry acetone and mixed with 335 mg of 2-phenoxy-thioacetamide. The mixture was stirred at room temperature for 6 h, the crystallized hydrobromide of the product was filtered off with suction and the residue was washed with acetone and dried under reduced pressure. The free base was obtained by introducing the salt into a mixture of 30 ml of ethyl acetate and 20 ml of saturated sodium bicarbonate solution and stirring for 20 mins. The organic phase was separated off, washed with saturated sodium fluoride solution and dried over magnesium sulfate. The mixture was filtered and the filtrate was concentrated under reduced pressure. The concentrated product yielded was 6-chloro-2-phenoxymethyl-8,8a-dihydroindeno[1,2-d]thiazol-3a-ol having a melting point of 121° C.

PREPARATION EXAMPLE 2

EXAMPLE 2 (Compound 6)

Synthesis of 6-Chloro-2-(2,4-dichlorophenoxymethyl)-8,8a-dihydroindeno[1,2-d]thiazol-3a-ol Hydrobromide At room temperature, 0.25 g of 2-bromo-5-chloroindan-1-on and 0.24 g of 2-(2,4-dichlorophenoxy)-thioacetamide ware dissolved in 5 ml of dry acetone, and the mixture was stirred at room temperature for 12 h. The resulting precipitate was filtered off with suction, washed with acetone and dried under high vacuum. This yielded the hydrobromide of 6-chloro-2-(2, 4-dichlorophenoxymethyl)-8,8a-dihydroindeno[1,2-d]thiazol-3a-ol having a melting point of 170° C. (decomposition).

PREPARATION EXAMPLE 3

EXAMPLE 3 (Compound 9)

Synthesis of 2-(4-tert-butylphenoxymethyl)-6-chloro-8,8a-dihydroindeno [1,2-d]thiazol-3a-ol At room temperature, 0.49 g of 2-bromo-5-chlorindan-1-on and 0.45 g of 2-(4-tert-butylphenoxy)-thioacetamide were dissolved in 10 ml of dry acetone, and the mixture was stirred at room temperature for 12 h. The precipitated hydrobromide was filtered off with suction and washed with acetone. The residue was suspended in a little ethyl acetate and treated with saturated sodium bicarbonate solution. The organic phase was separated off, dried over magnesium sulfate, filtered and concentrated under reduced pressure. This synthesis yielded 2-(4-tert-butylphenoxymethyl)-6-chloro-8,8a-dihydroindeno [1,2-d]thiazol-3a-ol having a melting point of 122–124° C.

PREPARATION EXAMPLE 4

EXAMPLE 4 (Compound 12)

Synthesis of 2-Benzylsulfanylmethyl-6-chloro-8,8a-dihydroindeno [1,2-d]thiazol-3a-ol a) 2-benzylsulfanyl-thioacetamide:

At room temperature, 1.2 g of benzylsulfanyl-acetonitrile were dissolved in 10 ml of dry ethanol and mixed with 1.25 ml of diethyl dithiophosphate, and the mixture was stirred at reflux for 6 h. The cooled reaction solution was concentrated under reduced pressure and purified chromatographically over silica gel using ethyl acetate/n-heptane ½. The resulting 2-benzylsulfanyl-thioacetamide was used for the next step.

b) 2-benzylsulfanylmethyl-6-chloro-8,8a-dihydroindeno[1,2-d]thiazol-3a-ol:

At room temperature, 0.54 g of 2-benzylsulfanyl-thioacetamide were dissolved in 10 ml of dry acetone and mixed with 0.67 g of 2-bromo-5-chlorindan-1-on, and the mixture was stirred at room temperature for 4 h. The resulting precipitate was filtered off with suction, washed with acetone, taken up in ethyl acetate, mixed with saturated sodium bicarbonate solution and extracted twice. The organic phase was dried over magnesium sulfate, filtered and concentrated under reduced pressure. This synthesis yielded 2-benzylsulfanylmethyl-6-chloro-8,8a-dihydroindeno[1,2-d]thiazol-3a-ol having a melting point of 102–104° C.

What is claimed is:

1. A compound of formula I:

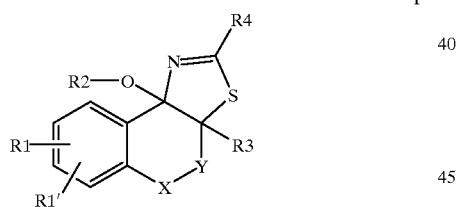

I wherein:

Y is selected from the group consisting of a direct bond, $-CH_2-$, and $-CH_2-CH_2-$;

X is selected from the group consisting of $CH_2$, $CH(CH_3)$, $CH(C_2H_5)$, $CH(C_3H_7)$, and $CH(C_6H_5)$;

R1, R1' are independently selected from the group consisting of H, F, Cl, Br, I, $CF_3$, $NO_2$, CN, COOH, $COO(C_1-C_6)$alkyl, $CONH_2$, $CONH(C_1-C_6)$alkyl, $CON[(C_1-C_6)alkyl]_2$, $(C_1-C_6)$-alkyl, $(C_2-C_6)$-alkenyl, $(C_2-C_6)$-alkynyl, $O-(C_1-C_6)$-alkyl, wherein one or more of the hydrogens in the alkyl moieties may be optionally replaced by fluorine, or a hydrogen may be optionally replaced by OH, $OC(O)CH_3$, $OC(O)H$, $O-CH_2-Ph$, $NH_2$, $NH-CO-CH_3$ or $N(COOCH_2Ph)_2$, $SO_2-NH_2$, $SO_2NH(C_1-C_6)$-alkyl, $SO_2N[(C_1-C_6)-alkyl]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, where n is 0–6 and wherein the phenyl radical is optionally substituted in up to two positions by F, Cl, Br, OH, $CF_3$, $NO_2$, CN, $OCF_3$, $O-(C_1C_6)$-alkyl, $(C_1-C_6)$-alkyl, or $NH_2$;

$NH_2$, $NH-(C_1-C_6)$-alkyl, $N((C_1-C_6)$-alkyl$)_2$, $NH(C_1-C_7)$-acyl, phenyl, biphenyl, $O-(CH_2)_n$-phenyl, where n is 0–6, 1- or 2-naphthyl, 2-, 3- or 4-pyridyl, 2-or 3-furanyl, 2- or 3-thienyl, wherein the phenyl, biphenyl, naphthyl, pyridyl, furanyl or thienyl rings may be independently optionally substituted up to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, or $CONH_2$;

1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;

R2 is selected from the group consisting of H, $(C_1-_6)$-alkyl, $(C_3-C_6)$-cycloalkyl, $(CH_2)_{n'}$-phenyl, $(CH_2)_{n'}$-thienyl, $(CH_2)_{n'}$-pyridyl, $(CH_2)_{n'}$-furyl, $C(O)-(C_1-C_6)$-alkyl, $C(O)-(C_3-C_6)$-cycloalkyl, $C(O)-(CH_2)_{n'}$-phenyl, $C(O)-(CH_2)_{n'}$-thienyl, $C(O)-(CH_2)_{n'}$-pyridyl and $C(O)-(CH_2)_{n'}$-furyl, where n' is 0–5, wherein the phenyl, thienyl, pyridyl, or furyl ring may be optionally substituted up to two times by Cl, F, CN, $CF_3$, $(C_1-C_3)$-alkyl, OH or $O-(C_1-C_6)$-alkyl;

R3 is selected from the group consisting of H, $(C_1-C_6)$-alkyl, F, CN, $N_3$, $O-(C_1-C_6)$-alkyl, $(CH_2)_{n'}$-phenyl, $(CH_2)_{n'}$-thienyl, $(CH_2)_{n'}$-pyridyl and $(CH_2)_{n'}$-furyl, where n' is 0–5, wherein the phenyl, thienyl, pyridyl, or furyl ring may be optionally substituted up to two times by Cl, F, CN, $CF_3$, $(C_1-C_3)$-alkyl, OH or $O-(C_1-C_6)$-alkyl, $(C_2-C_6)$-alkynyl, $(C_2-C_6)$-alkenyl, $C(O)OCH_3$, $C(O)OCH_2CH_3$, $C(O)OH$, $C(O)NH_2$, $C(O)NHCH_3$, $C(O)N(CH_3)_2$, or $OC(O)CH_3$;

R4 is selected from the group consisting of $(C_8-C_6)$-cycloalkyl, wherein one or more hydrogens of the alkyl moiety may be optionally replaced by fluorine, or a hydrogen may be optionally replaced by OH, $OC(O)CH_3$, $OC(O)H$, $O-CH_2-Ph$ or $O-(C_1-C_4)$-alkyl;

$(CH_2)_{n''}-A-R8$, where n'' is 1–6, except for when $(CH_2)_{n''}-A-R8$ is $-CH_2-O-CH_2$-phenyl, then the phenyl moiety is unsubstituted; and $(CH_2)_r-B-R9$, where r is 1–6;

A is selected from the group consisting of O, S, SO and $SO_2$;

B is selected from the group consisting of NH, $N-(C_1-_6)$-alkyl, NCHO and $N(CO-CH_3)$;

R8 is selected from the group consisting of $(C_5-C_{24})$-alkyl, $(C_3-C_{10})$-cycloalkyl, wherein one or more hydrogens of the alkyl radical may be optionally replaced by fluorine, or a hydrogen may be optionally replaced by OH, $OC(O)CH_3$, $OC(O)H$, $O-CH_2-Ph$ or $O-(C_1-C_4)$-alkyl; and $(CH_2)_m$-aryl, where m is 0–6 and aryl is selected from the group consisting of phenyl, naphthyl, biphenyl, thienyl and pyridyl;

wherein the aryl moiety may be optionally substituted up to two times by F, Cl, Br, OH, $CF_3$, $NO_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, SO$_2$—NH$_2$, SO$_2$—NH(C$_1$–C$_8$-alkyl), SO$_2$—N(C$_1$–C$_8$-alkyl)$_2$, SO$_2$—NH(C$_3$–C$_8$-cycloalkyl), SO$_2$—N(C$_3$–C$_8$-cycloalkyl)$_2$, (CH$_2$)$_{m'}$—SO$_2$—NH$_2$, (CH$_2$)$_m$—SO$_2$—NH—(C$_1$–C$_6$)-alkyl, (CH$_2$)$_{m'}$—SO$_2$—N((C$_1$–C$_6$)-alkyl)$_2$, where m' is 1–6, SO$_2$—N(=CH—N(CH$_3$)$_2$), (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH(C$_1$–C$_6$)-alkyl, N(C$_1$–C$_6$-alkyl)$_2$, NH—CO—(C$_1$–C$_6$)-alkyl, NH—CO—phenyl, NH—SO$_2$—(C$_1$–C$_8$-alkyl), N(C$_1$–C$_6$-alkyl)—SO$_2$—(C$_1$–C$_8$-alkyl), NH—SO$_2$-phenyl, wherein the phenyl ring may be optionally substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$, pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;

R9 is (CH$_2$)$_m$-aryl, where m is 0–6 and aryl is selected from the group consisting of phenyl, naphthyl, biphenyl, thienyl and pyridyl;

wherein the aryl moiety may be optionally substituted up to two times by F, Cl, Br, OH, CF$_3$, NO$_2$, CN, OCF$_3$, O—(C$_1$–C$_6$)-alkyl, S—(C$_1$–$_6$)-alkyl, SO—(C$_1$–C$_6$)-alkyl, SO$_2$—(C$_1$–C$_6$)-alkyl, SO$_2$—NH$_2$, SO$_2$—NH(C$_1$–C$_8$-alkyl), SO$_2$—N(C$_1$C$_8$-alkyl)$_2$, SO$_2$—NH(C$_3$–C$_8$-cycloalkyl), SO$_2$—N(C$_3$–C$_8$-cycloalkyl)$_2$, (CH$_2$)$_{m'}$—SO$_2$—NH$_2$, (CH$_2$)$_m$—SO$_2$—NH—(C$_1$–C$_6$)-alkyl, (CH$_2$)$_{m'}$—SO$_2$—N((C$_1$–C$_6$)-alkyl)$_2$, where m' is 1–6, SO$_2$—N(=CH—N(CH$_3$)$_2$), (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH(C$_1$–C$_6$)-alkyl, N(C$_1$–C$_6$-alkyl)$_2$, NH—CO—(C$_1$–C$_6$)-alkyl, NH—CO—phenyl, NH—SO$_2$—(C$_1$–C$_8$-alkyl), N(C$_1$–C$_6$-alkyl)—SO$_2$—(C$_1$–C$_8$-alkyl), NH—SO$_2$-phenyl, wherein the phenyl ring may be optionally substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$, pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, where p is 0–3;

and a physiologically acceptable salt thereof.

2. The compound of claim 1, wherein:

Y is a direct bond;

X is CH$_2$;

R1, R1' are independently selected from the group consisting of H, F, Cl, Br, I, CF$_3$, NO$_2$, CN, COOH, COO(C$_1$–C$_6$)alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, wherein one or more hydrogens of the alkyl radical may be optionally replaced by fluorine, or a hydrogen may be optionally replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl, where n is 0–6 and wherein the phenyl radical is optionally substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$;

NH$_2$, NH—(C$_{1-6}$)-alkyl, N((C$_1$–C$_6$)-alkyl)$_2$, NH(C$_1$–C$_7$)-acyl, phenyl, biphenyl, O—(CH$_2$)$_n$-phenyl, where n is 0–6, 1- or 2-naphthyl, 2-, 3- or 4-pyridyl, 2- or 3-furanyl, 2- or 3-thienyl, wherein the phenyl, biphenyl, naphthyl, pyridyl, furanyl or thienyl rings may be independently optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$;

1,2,3-triazol-5-yl, wherein the triazole ring may be optionally substituted in the 1-, 2- or 3-position by methyl or benzyl; and tetrazol-5-yl, wherein the tetrazole ring may be optionally substituted in the 1- or 2-position by methyl or benzyl;

R2 is selected from the group consisting of H, (C$_1$–C$_6$)-alkyl, (C$_3$–C$_6$)-cycloalkyl, (CH$_2$)$_{n'}$-phenyl, (CH$_2$)$_{n'}$-thienyl, (CH$_2$)$_{n'}$-pyridyl, (CH$_2$)$_{n'}$-furyl, C(O)—(C$_{1-6}$)-alkyl, C(O)—(C$_3$–C$_6$)-cycloalkyl, C(O)—(CH$_2$)$_{n'}$-phenyl, C(O)—(CH$_2$)$_{n'}$-thienyl, C(O)—(CH$_2$)$_{n'}$-pyridyl and C(O)—(CH$_2$)$_{n'}$-furyl, where n' is 0–5 and wherein the phenyl, thienyl, pyridyl or furyl ring may be independently optionally substituted up to two times by Cl, F, CN, CF$_3$, (C$_1$–C$_3$)-alkyl, OH or O—(C$_1$–C$_6$)-alkyl;

R3 is selected from the group consisting of H, (C$_1$–C$_6$)-alkyl, F, CN, N$_3$, O—(C$_1$–C$_6$)-alkyl, (CH$_2$)$_{n'}$-phenyl, (CH$_2$)$_{n'}$-thienyl, (CH$_2$)$_{n'}$-pyridyl, (CH$_2$)$_{n'}$-furyl, where n' is 0–5 and wherein the phenyl, thienyl, pyridyl or furyl ring may be independently optionally substituted up to two times by Cl, F, CN, CF$_3$, (C$_1$–C$_3$)-alkyl, OH or O—(C$_1$–C$_6$)-alkyl;

(C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$ and OC(O)CH$_3$;

R4 is selected from the group consisting of (C$_8$–C$_{16}$)-cycloalkyl, wherein one or more hydrogens of the alkyl radicals may be optionally replaced by fluorine, or a hydrogen may be optionally replaced by OH, OC(O)CH$_3$, OC(O)H, O—CH$_2$—Ph or O—(C$_1$–C$_4$)-alkyl;

(CH$_2$)$_{n''}$—A—R8, where n'' is 1–6, except for when (CH$_2$)$_{n''}$—A—R8 is —CH$_2$—O—CH$_2$-phenyl, then the phenyl is unsubstituted; and (CH$_2$)$_r$—B—R9, where r is 1–6;

A is selected from the group consisting of O, S, SO and SO$_2$;

B is selected from the group consisting of NH, N—(C$_{1-6}$)-alkyl, NCHO and N(CO—CH$_3$);

R8 is selected from the group consisting of (C$_5$–C$_{24}$)-alkyl, (C$_3$–C$_{10}$)-cycloalkyl, wherein one or more hydrogens of the alkyl radicals may be optionally replaced by fluorine, or a hydrogen may be optionally replaced by OH, OC(O)CH$_3$, OC(O)H, O—CH$_2$—Ph or O—(C$_1$–C$_4$)-alkyl; and (CH$_2$)$_m$-aryl, where m is 0–6 and aryl is selected from the group consisting of phenyl, naphthyl, biphenyl, thienyl and pyridyl, wherein the aryl moiety may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $SO_2$—$NH_2$, $SO_2$—NH$(C_1-C_8$-alkyl), $SO_2$—N$(C_1C_8$-alkyl$)_2$, $SO_2$—NH$(C_3-C_8$-cycloalkyl), $SO_2$—N$(C_3-C_8$-cycloalkyl$)_2$, $(CH_2)_m$—$SO_2$—$NH_2$, $(CH_2)_{m'}$—$SO_2$—NH—$(C_1-C_6)$-alkyl, $(CH_2)_{m'}$—$SO_2$—N$((C_1-C_6)$-alkyl$)_2$, where m' is 1–6, $SO_2$—N(=CH—N$(CH_3)_2$), $(C_1-C_6)$-alkyl, $(C_3-C_6)$-cycloalkyl, COOH, COO$(C_1-C_6)$alkyl, COO$(C_3-C_6)$cycloalkyl, $CONH_2$, CONH$(C_{1-6})$alkyl, CON$[(C_1-C_6)$alkyl$]_2$, CONH$(C_3-C_6)$cycloalkyl, $NH_2$, NH$(C_{1-6})$-alkyl, N$(C_1-C_6$-alkyl$)_2$, NH—CO—$(C_{1-6})$-alkyl, NH—CO—phenyl, NH—$SO_2$—$(C_1-C_8$-alkyl), N$(C_1-C_6$-alkyl)—$SO_2$—$(C_1-C_8$-alkyl), NH—$SO_2$-phenyl,
wherein the phenyl ring may be optionally substituted up to two times by F, Cl, CN, OH, $(C_{1-6})$-alkyl, O—$(C_1-C_6)$-alkyl, $CF_3$, COOH, COO$(C_1-C_6)$-alkyl or $CONH_2$;
pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, where p is 0–3;
R9 is $(CH_2)_m$-aryl, where m can be 0–6 and aryl is selected from the group consisting of phenyl, naphthyl, biphenyl, thienyl and pyridyl,
wherein the aryl moiety may be optionally substituted up to two times by F, Cl, Br, OH, $CF_3$, $NO_2$, CN, $OCF_3$, O—$(C_{1-6})$-alkyl, S—$(C_1-C_6)$-alkyl, SO—$(C_1-C_6)$-alkyl, $SO_2$—$(C_1-C_6)$-alkyl, $SO_2$—$NH_2$, $SO_2$—NH$(C_1-C_8$-alkyl), $SO_2$—N$(C_1-C_8$-alkyl$)_2$, $SO_2$—NH$(C_3-C_8$-cycloalkyl), $SO_2$—N$(C_3-C_8$-cycloalkyl$)_2$, $(CH_2)_{m'}$—$SO_2$—$NH_2$, $(CH_2)_{m'}$—$SO_2$—NH—$(C_1-C_6)$-alkyl, $(CH_2)_{m'}$ $SO_2$—N$((C_1-C_6)$-alkyl$)_2$, where m' is 1–6, $SO_2$—N (=CH—N$(CH_3)_2$), $(C_1-C_6)$-alkyl, $(C_3-C_6)$-cycloalkyl, COOH, COO$(C_{1-6})$alkyl, COO$(C_3-C_6)$cycloalkyl, $CONH_2$, CONH$(C_1-C_6)$alkyl, CON$[(C_{1-6})$alkyl$]_2$, CONH$(C_3-C_6)$cycloalkyl, $NH_2$, NH$(C_1-C_6)$-alkyl, N$(C_{1-6}$-alkyl$)_2$, NH—CO—$(C_1-C_6)$-alkyl, NH—CO-phenyl, NH—$SO_2$—$(C_1-C_8$-alkyl), N$(C_{1-6}$-alkyl)—$SO_2$—$(C_1-C_8$-alkyl), NH—$SO_2$-phenyl,
wherein the phenyl ring may be optionally substituted up to two times by F, Cl, CN, OH, $(C_1-C_6)$-alkyl, O—$(C_1-C_6)$-alkyl, $CF_3$, COOH, COO$(C_1-C_6)$-alkyl or $CONH_2$;
pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, where p is 0–3;
and a physiologically acceptable salt thereof.

3. The compound of claim 1, wherein:
Y is a direct bond;
x is $CH_2$;
R1, R1' are independently selected from the group consisting of H, F, Cl, Br, I, $CF_3$, $NO_2$, CN, COOH, COO$(C_1-C_6)$alkyl, $CONH_2$, CONH$(C_1-C_6)$alkyl, CON$[(C_1-C_6)$alkyl$]_2$, $(C_1-C_6)$-alkyl, $(C_2-C_6)$-alkenyl, $(C_2-C_6)$-alkynyl, O—$(C_1-C_6)$-alkyl,
wherein one or more hydrogens of the alkyl radicals may be optionally replaced by fluorine,
or a hydrogen may be optionally replaced by OH, $OC(O)CH_3$, $OC(O)H$, O—$CH_2$—Ph, $NH_2$, NH—CO—$CH_3$ or N$(COOCH_2Ph)_2$;

$SO_2$—$NH_2$, $SO_2$NH$(C_1-C_6)$-alkyl, $SO_2$N$[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl, $SO_2$—$(CH_2)_n$-phenyl,
where n is 0–6 and wherein the phenyl radical is optionally substituted up to two times by F, Cl, Br, OH, $CF_3$, $NO_2$, CN, $OCF_3$, O—$(C_1-C_6)$-alkyl, $(C_1-C_6)$-alkyl or $NH_2$;
$NH_2$, NH—$(C_1-C_6)$-alkyl, N$((C_1-C_6)$-alkyl$)_2$, NH$(C_{1-7})$-acyl, phenyl, biphenyl, O—$(CH_2)_n$-phenyl, where n can be 0–6, 1- or 2-naphthyl, 2-, 3- or 4-pyridyl, 2- or 3-furanyl, 2- or 3-thienyl,
wherein the phenyl, biphenyl, naphthyl, pyridyl, furanyl or thienyl rings may be independently optionally substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_{1-6})$-alkyl, N$((C_1-C_6)$-alkyl$)_2$, $SO_2$—$CH_3$, COOH, COO—$(C_1-C_6)$-alkyl, $CONH_2$;
1,2,3-triazol-5-yl, wherein the triazole ring may be optionally substituted in the 1-, 2- or 3-position by methyl or benzyl; and
tetrazol-5-yl, wherein the tetrazole ring may be optionally substituted in the 1- or 2-position by methyl or benzyl;
R2 is selected from the group consisting of H, $(C_{1-6})$-alkyl, $(C_3-C_6)$-cycloalkyl, $(CH_2)_{n'}$-phenyl, $(CH_2)_{n'}$-thienyl, $(CH_2)_{n'}$-pyridyl, $(CH_2)_{n'}$-furyl, C(O)—$(C_1-C_6)$-alkyl, C(O)—$(C_3-C_6)$-cycloalkyl, C(O)—$(CH_2)_{n'}$-phenyl, C(O)—$(CH_2)_{n'}$-thienyl, C(O)—$(CH_2)_{n'}$-pyridyl and C(O)—$(CH_2)_{n'}$-furyl,
where n' is 0–5, and wherein the phenyl, thienyl, pyridyl or furyl ring may be independently optionally substituted up to two times by Cl, F, CN, $CF_3$, $(C_1-C_3)$-alkyl, OH, O—$(C_1-C_6)$-alkyl;
R3 is selected from the group consisting of H and F;
R4 is selected from the group consisting of $(C_8-C_{16})$-cycloalkyl,
wherein one or more hydrogens of the alkyl radicals may be optionally replaced by fluorine,
or a hydrogen may be optionally replaced by OH, $OC(O)CH_3$, $OC(O)H$, O—$CH_2$—Ph or O—$(C_1-C_4)$-alkyl;
$(CH_2)_{n''}$—A—R8, where n" is 1–6, except for when $(CH_2)_{n''}$—A—R8 is —$CH_2$—O—$CH_2$-phenyl, then the phenyl is unsubstituted; and
$(CH_2)_r$—B—R9, where r is 1–6;
A is selected from the group consisting of O and S;
B is selected from the group consisting of NH, N—$(C_1-C_6)$-alkyl, NCHO and N(CO—$CH_3$);
R8 is selected from the group consisting of $(C_5-C_{24})$-alkyl, $(C_3-C_{10})$-cycloalkyl,
wherein one or more hydrogens of the alkyl radicals may be optionally replaced by fluorine,
or a hydrogen may be optionally replaced by OH, $OC(O)CH_3$, $OC(O)H$, O—$CH_2$—Ph or O—$(C_1-C_4)$-alkyl; and
$(CH_2)_m$-aryl, where m is 0–6 and aryl is selected from the group consisting of phenyl, naphthyl, biphenyl, thienyl and pyridyl;
wherein the aryl moiety may be optionally substituted up to two times by F, Cl, Br, OH, $CF_3$, $NO_2$, CN, $OCF_3$, O—$(C_{1-6})$-alkyl, S—$(C_1-C_6)$-alkyl, SO—$(C_1-C_6)$-alkyl, $SO_2$—$(C_1-C_6)$-alkyl, $SO_2$—$NH_2$, $SO_2$—NH$(C_1-C_8$-alkyl), $SO_2$—N$(C_1-C_8$-alkyl$)_2$, $SO_2$—NH$(C_3-C_8$-cycloalkyl), $SO_2$—N$(C_3-C_8$-cycloalkyl$)_2$, $(CH_2)_{m'}$—$SO_2$—$NH_2$, $(CH_2)_{m'}$—$SO_2$—NH—$(C_1-C_6)$-alkyl, $(CH_2)_{m'}$—$SO_2$—N$((C_1-C_6)$-alkyl$)_2$, where m' is 1–6, $SO_2$—N(=CH—N(CH$_3$)$_2$), $(C_1-C_6)$-alkyl, $(C_3-C_6)$-cycloalkyl, COOH, COO($C_1-C_6$)alkyl, COO($C_3-C_6$)cycloalkyl, CONH$_2$, CONH($C_1-C_6$) alkyl, CON[($C_1-C_6$)alkyl]$_2$, CONH($C_3-C_6$) cycloalkyl, NH$_2$, NH($C_1-C_6$)-alkyl, N($C_1-C_6$-alkyl)$_2$, NH—CO—($C_1-C_6$)-alkyl, NH—CO—phenyl, NH—SO$_2$—($C_1-C_8$-alkyl), N($C_1-C_6$-alkyl)—SO$_2$—($C_1-C_8$-alkyl), NH—SO$_2$-phenyl,
  wherein the phenyl ring may be optionally substituted up to two times by F, Cl, CN, OH, $(C_1-C_6)$-alkyl, O—$(C_1-C_6)$-alkyl, CF$_3$, COOH, COO($C_1-C_6$)-alkyl or CONH$_2$;
  pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or SO$_2$—$(CH_2)_p$-phenyl, where p is 0–3;
R9 is $(CH_2)_m$-aryl, where m is 0–6 and aryl is selected from the group consisting of phenyl, naphthyl, biphenyl, thienyl and pyridyl;
  wherein the aryl moiety may be optionally substituted up to two times by F, Cl, Br, OH, CF$_3$, NO$_2$, CN, OCF$_3$, O—$(C_1-C_6)$-alkyl, S—$(C_1-C_6)$-alkyl, SO—$(C_1-C_6)$-alkyl, SO$_2$—$(C_1-C_6)$-alkyl, SO$_2$—NH$_2$, SO$_2$—NH($C_1-C_8$-alkyl), SO$_2$—N($C_1-C_8$-alkyl)$_2$, SO$_2$—NH($C_3-C_8$-cycloalkyl), SO$_2$—N($C_3-C_8$-cycloalkyl)$_2$, $(CH_2)_{m'}$—SO$_2$—NH$_2$, $(CH_2)_{m'}$—SO$_2$—NH—($C_1-C_6$)-alkyl, $(CH_2)_{m'}$—SO$_2$—N(($C_1-C_6$)-alkyl)$_2$, where m' can be 1–6, SO$_2$—N(=CH—N(CH$_3$)$_2$), $(C_1-C_6)$-alkyl, $(C_3-C_6)$-cycloalkyl, COOH, COO($C_1-C_6$)alkyl, COO($C_3-C_6$)cycloalkyl, CONH$_2$, CONH($C_{1-6}$) alkyl, CON[($C_1-C_6$)alkyl]$_2$, CONH($C_3-C_6$) cycloalkyl, NH$_2$, NH($C_1-C_6$)-alkyl, N($C_1-C_6$-alkyl)$_2$, NH—CO—($C_{1-6}$)-alkyl, NH—CO—phenyl, NH—SO$_2$—($C_1-C_8$-alkyl), N($C_1-C_6$-alkyl)—SO$_2$—($C_1-C_8$-alkyl), NH—SO$_2$-phenyl,
  wherein the phenyl ring may be optionally substituted up to two times by F, Cl, CN, OH, $(C_1-C_6)$-alkyl, O—$(C_1-C_6)$-alkyl, CF$_3$, COOH, COO($C_1-C_6$)-alkyl or CONH$_2$;
  pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or SO$_2$—$(CH_2)_p$-phenyl, where p is 0–3;
and a physiologically acceptable salt thereof.

4. The compound of claim 1, wherein:
Y is a direct bond;
x is CH$_2$;
R1, R1' are independently selected from the group consisting of H, F, Cl, Br, I and $(C_1-C_6)$-alkyl;
R2 is selected from the group consisting of H and $(C_1-C_6)$-alkyl;
R3 is selected from the group consisting of H and F;
R4 is selected from the group consisting of $(C_8-C_{,6})$-cycloalkyl and $(CH_2)_{n''}$—A—R8, where n" is 1–6, except when $(CH_2)_{n''}$—A—R8 is —CH$_2$—O—CH$_2$-phenyl, then the phenyl is unsubstituted;
A is selected from the group consisting of O and S;
R8 is selected from the group consisting of $(C_5-C_{24})$-alkyl and $(CH_2)_m$-aryl, where m is 0–6 and aryl is phenyl;
  wherein the aryl moiety may be optionally substituted up to two times by F, Cl, Br, OH, CF$_3$, NO$_2$, CN, OCF$_3$, O—$(C_1-C_6)$-alkyl, S—$(C_1-C_6)$-alkyl, SO—$(C_1C_6)$-alkyl, SO$_2$—$(C_1-C_6)$-alkyl, SO$_2$—NH$_2$, SO$_2$—NH($C_1-C_8$-alkyl), SO$_2$—N($C_1-C_8$-alkyl)$_2$, SO$_2$—NH($C_3-C_8$-cycloalkyl), SO$_2$—N($C_3C_8$-cycloalkyl)$_2$, $(CH_2)_{m'}$—SO$_2$—NH$_2$, $(CH_2)_{m'}$—SO$_2$—NH—($C_1-C_6$)-alkyl, $(CH_2)_{m'}$—SO$_2$—N(($C_1-C_6$)-alkyl)$_2$, where m' is 1–6, SO$_2$—N(=CH—N(CH$_3$)$_2$), $(C_1-C_6)$-alkyl, $(C_3-C_6)$-cycloalkyl, COOH, COO($C_1-C_6$)alkyl, COO($C_3-C_6$)cycloalkyl, CONH$_2$, CONH($C_1-C_6$) alkyl, CON[($C_1-C_6$)alkyl]$_2$, CONH($C_3-C_6$) cycloalkyl, NH$_2$, NH($C_1-C_6$)-alkyl, N($C_1-C_6$-alkyl)$_2$, NH—CO—($C_1-C_6$)-alkyl, NH—CO—phenyl, NH—SO$_2$—($C_1-C_8$-alkyl), N($C_1-C_6$-alkyl)—SO$_2$—($C_1-C_8$-alkyl), NH—SO$_2$-phenyl,
  wherein the phenyl ring may be optionally substituted up to two times by F, Cl, CN, OH, $(C_1-C_6)$-alkyl, O—$(C_1-C_6)$-alkyl, CF$_3$, COOH, COO($C_1-C_6$)-alkyl or CONH$_2$;

10 pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or SO$_2$—$(CH_2)_p$-phenyl, where p is 0–3;
and a physiologically acceptable salt thereof.

5. A pharmaceutical composition comprising one or more of the compounds as claimed in claim 1 and a pharmaceutically acceptable carrier.

6. A pharmaceutical composition comprising one or more of the compounds as claimed in claim 1 and one or more anorectic active preparations and a pharmaceutically acceptable carrier.

7. A method for the treatment of obesity comprising administering to a patient in need thereof an effective amount of a compound as claimed in claim 1.

8. A method for the treatment of type II diabetes comprising administering to a patient in need thereof an effective amount of a compound as claimed in claim 1.

9. A method for the treatment of obesity comprising administering to a patient in need thereof an effective amount of a compound as claimed in claim 1 and further administering at least one further anorectic active compound.

10. A method for the treatment of type II diabetes comprising administering to a patient in need thereof an effective amount of a compound as claimed in claim 1 and farther administering at least one farther anorectic active compound.

11. A process for preparing a pharmaceutical comprising one or more compounds as claimed in claim 1, which comprises mixing the active compound with a pharmaceutically suitable vehicle and bringing this mixture into a form suitable for administration.

12. A pharmaceutical composition comprising one or more of the compounds as claimed in claim 2 and a pharmaceutically acceptable carrier.

13. A pharmaceutical composition comprising one or more of the compounds as claimed in claim 2 and one or more anorectic active preparations and a pharmaceutically acceptable carrier.

14. A method for the treatment of obesity comprising administering to a patient in need thereof an effective amount of a compound as claimed in claim 2.

15. A method for the treatment of type II diabetes comprising administering to a patient in need thereof an effective amount of a compound as claimed in claim 2.

16. A method for the treatment of obesity comprising administering to a patient in need thereof an effective amount of a compound as claimed in claim 2 and further administering at least one further anorectic active compound.

17. A method for the treatment of type II diabetes comprising administering to a patient in need thereof an effective amount of a compound as claimed in claim 2 and further administering at least one further anorectic active compound.

18. A process for preparing a pharmaceutical comprising one or more compounds as claimed in claim 2, which comprises mixing the active compound with a pharmaceutically suitable vehicle and bringing this mixture into a form suitable for administration.

19. A pharmaceutical composition comprising one or more of the compounds as claimed in claim 3 and a pharmaceutically acceptable carrier.

20. A pharmaceutical composition comprising one or more of the compounds as claimed in claim 3 and one or more anorectic active preparations and a pharmaceutically acceptable carrier.

21. A method for the treatment of obesity comprising administering to a patient in need thereof an effective amount of a compound as claimed in claim 3.

22. A method for the treatment of type II diabetes comprising administering to a patient in need thereof an effective amount of a compound as claimed in claim 3.

23. A method for the treatment of obesity comprising administering to a patient in need thereof an effective amount of a compound as claimed in claim 3 and further administering at least one further anorectic active compound.

24. A method for the treatment of type II diabetes comprising administering to a patient in need thereof an effective amount of a compound as claimed in claim 3 and further administering at least one further anorectic active compound.

25. A process for preparing a pharmaceutical comprising one or more compounds as claimed in claim 3, which comprises mixing the active compound with a pharmaceutically suitable vehicle and bringing this mixture into a form suitable for administration.

26. A pharmaceutical composition comprising one or more of the compounds as claimed in claim 4 and a pharmaceutically acceptable carrier.

27. A pharmaceutical composition comprising one or more of the compounds as claimed in claim 4 and one or more anorectic active preparations and a pharmaceutically acceptable carrier.

28. A method for the treatment of obesity comprising administering to a patient in need thereof an effective amount of a compound as claimed in claim 4.

29. A method for the treatment of type II diabetes comprising administering to a patient in need thereof an effective amount of a compound as claimed in claim 4.

30. A method for the treatment of obesity comprising administering to a patient in need thereof an effective amount of a compound as claimed in claim 4 and further administering at least one further anorectic active compound.

31. A method for the treatment of type II diabetes comprising administering to a patient in need thereof an effective amount of a compound as claimed in claim 4 and further administering at least one further anorectic active compound.

32. A process for preparing a pharmaceutical comprising one or more compounds as claimed in claim 4, which comprises mixing the active compound with a pharmaceutically suitable vehicle and bringing this mixture into a form suitable for administration.

33. A process for preparing the compounds as claimed in claim 1, which comprises reacting, according to the formula scheme below,

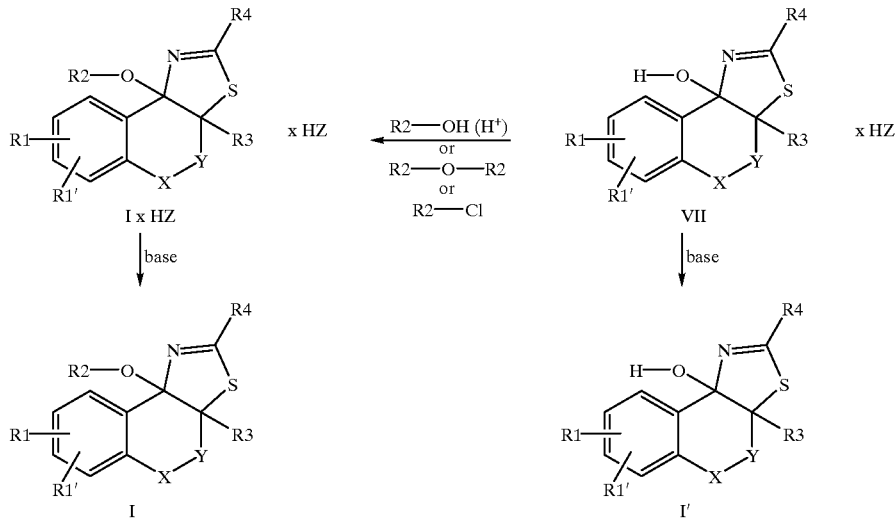

a compound of the formula VII in which X, Y, R1, R1', R3 and R4 are as defined in claim 1, either with a base to give compound I' in which R2 is hydrogen or with one of the compounds R2-OH, R2-O—R2 or R2-Cl in which R2 is as defined in claim 1 to give a compound of the formula I×HZ, which is then reacted further with a base to yield the compound of the formula I.

* * * * *